(12) United States Patent
Sylvester et al.

(10) Patent No.: US 10,192,030 B2
(45) Date of Patent: Jan. 29, 2019

(54) METHODS FOR ACCURATELY MEASURING ENZYME ACTIVITY

(71) Applicants: Juliesta Elaine Sylvester, San Diego, CA (US); Stephen Joseph Kron, Oak Park, IL (US)

(72) Inventors: Juliesta Elaine Sylvester, San Diego, CA (US); Stephen Joseph Kron, Oak Park, IL (US)

(*) Notice: Subject to any disclaimer, the term of this patent is extended or adjusted under 35 U.S.C. 154(b) by 0 days.

(21) Appl. No.: 15/699,283

(22) Filed: Sep. 8, 2017

(65) Prior Publication Data

US 2018/0032672 A1 Feb. 1, 2018

Related U.S. Application Data

(63) Continuation of application No. 12/660,608, filed on Mar. 1, 2010, now abandoned.

(60) Provisional application No. 61/208,925, filed on Mar. 2, 2009.

(51) Int. Cl.
*G01N 33/48* (2006.01)
*G06F 19/24* (2011.01)

(52) U.S. Cl.
CPC .................................. *G06F 19/24* (2013.01)

(58) Field of Classification Search
CPC ........................................................ C12Q 1/10
USPC ............................... 702/19, 20, 26; 435/7.92
See application file for complete search history.

(56) References Cited

U.S. PATENT DOCUMENTS

| | | |
|---|---|---|
| 5,981,201 A | 11/1999 | Avraham et al. |
| 6,244,121 B1 | 6/2001 | Hunter |
| 6,942,987 B2 | 9/2005 | Auld |
| 7,674,580 B2 | 3/2010 | Saba et al. |
| 7,764,580 B2 | 7/2010 | Ueno |
| 8,361,738 B2 * | 1/2013 | Kartalov ........... B01L 3/502738 435/7.94 |
| 2001/0026920 A1 | 10/2001 | Chandler et al. |
| 2005/0118574 A1 | 6/2005 | Chandler et al. |
| 2006/0088894 A1 | 4/2006 | Wright et al. |
| 2007/0196860 A1 | 8/2007 | Gee et al. |
| 2007/0238141 A1 | 10/2007 | Notoya et al. |
| 2007/0264665 A1 | 11/2007 | Akhavan-Tafti |
| 2008/0312260 A1 | 12/2008 | Haley et al. |
| 2009/0258377 A1 * | 10/2009 | Ferreras Gomez ...... C12Q 1/00 435/7.92 |
| 2009/0281113 A1 | 11/2009 | Gathmann et al. |

OTHER PUBLICATIONS

Snyder and Kirkland, Introduction to Modern Liquid Chromatography, 2nd Ed. (New York: John Wiley and Sons, Inc., 1979), pp. 571-572.
Mathews et al., Biochemistry, 3rd Ed. (San Francisco: Addison Wesley Longman, Inc., 2000) pp. 128, 360, 369.

(Continued)

*Primary Examiner* — Larry D Riggs, II
(74) *Attorney, Agent, or Firm* — Grant IP, Inc.

(57) ABSTRACT

Provided are biological methods for measuring enzyme activity. The methods include generating reactions, and contacting each reaction generated with a set of internal standards, where each of the internal standards includes a different amount of product. The methods also include generating a standard curve for each of the reactions from the internal standards in each of the reactions.

28 Claims, 10 Drawing Sheets

(56) References Cited

OTHER PUBLICATIONS

Bernsteel, D. J., D. L. Roman, et al. (2008). "In vitro protein kinase activity measurement by flow cytometry." Anal Biochem 383(2): 180-5.

Hanley, B. (2007). "Variance in multiplex suspension array assays: intraplex method improves reliability." Theor Biol Med Model 4: 32.

Kirchmer C. J., Winter, M. C., et al. (1983). "Factors affecting the accuracy of quantitative analyses of priority pollutants using GC/MS." Environ. Sci. Technol. 17: 396-40.

Koren, A., I. Tirosh, et al. (2007). "Autocorrelation analysis reveals widespread spatial biases in microarray experiments." BMC Genomics 8: 164.

Livak, K. J., Schmittgen, T. D. (2001). "Analysis of relative gene expression data using real-time quantitative PCR and the 2-delta delta CT method." Methods 25: 402-408.

Martins, T. B. (2002). "Development of internal controls for the Luminex instrument as part of a multiplex . . . antibody profile." Clin Diagn Lab Immunol 9(1): 41-5.

Perez, 0. D. and G. P. Nolan (2002). "Simultaneous measurement of multiple active kinase states using polychromatic flow cytometry." Nat Biotechnol 20(2): 155-62.

Shults, M. D., I. A. Kozlov, et al. (2007). "A multiplexed protein kinase assay." Chembiochem 8(8): 933-42.

Xiaoming, H., S. Syuhei, et al. (2008). "A quantitative peptide array for evaluation of protein kinase activity." Anal Biochem 372(1): 106-15.

Zhang, J. H., T. D. Chung, et al. (1999). "A Simple Statistical Parameter for Use in Evaluation and Validation of High Throughput Screening Assays." J Biomol Screen 4(2): 67-7.

Bence et al., "Direct stimulation of Bruton's tyrosine kinase by G(q)-protein alpha-subunit" Nature (1997) 389(6648):296-9.

Busman et al., "Identification of phosphorylation sites in phosphopeptides by positive and negative mode electrospray ionization-tandem mass spectrometry" J Am Soc Mass Spectrom (1996) 7:243-249.

Du et al., "Bead-based profiling of tyrosine kinase phosphorylation identifies SRC as a potential target for glioblastoma therapy" Nat Biotechnol (2009) 27:77-83.

Federighi, "Extended tables of the percentage points of student's t-distribution" J Am Stat Assoc (1959) 68:683-691.

Fulton et al., "Advanced multiplexed analysis with the FlowMetrix system" Clin Chem (1997) 43(9):1749-1756.

Giavedoni et al., "Simultaneous detection of multiple cytokines and chemokines from nonhuman primates using luminex technology" J Immunol Methods (2005) 301:89-101.

Henderson et al., "Functional peptide arrays for high-throughput chemical biology based applications" Curr Opin Biotechnol (2007) 18(4):326-330.

Houseman et al., "Peptide chips for the quantitative evaluation of protein kinase activity" Nat Biotechnol (2002) 20(3):270-4.

Ong et al., "Stable isotope labeling by amino acids in cell culture, SILAC, as a simple and accurate approach to expression proteomics" Mol Cell Proteomics (2002) 1:376-386.

Owen, "The power of student's t-test" J Amer Stat Assoc (1965) 60(309):320-333.

Robinson et al., "The protein tyrosine kinase family of the human genome" Oncogene (2000) 19(49):5548-57.

Songyang et al., "Catalytic specificity of protein-tyrosine kinases is critical for selective signaling" Nature (1995) 373(6514):536-9.

Wu et al., "A solid-phase Bcr-Abl kinase assay in 96-well hydrogel plates" Anal Biochem (2008) 375:18-26.

Wu et al., "Assaying Bcr-Abl kinase activity and inhibition in whole cell extracts by phosphorylation of substrates immobilized on agarose beads" Anal Biochem (2005) 347:67-76.

Yamadori et al., "Bruton's tyrosine kinase activity is negatively regulated by Sab, the Btk-SH3 domain-binding protein" PNAS USA (1999) 96(11):6341-6.

\* cited by examiner

Tyrosine Kinase Activity Assay
Phosphorylation 50%

| | Well | n Bead Count | X Florescence Intensity Median | Mean | SD Standard Deviation | SE Standard Error | Level of Confidence in Mean, at .01 level Interval | Min | Max |
|---|---|---|---|---|---|---|---|---|---|
| 1 | A1 | 119 | 24,838 | 23,014.6 | 6,509.5 | 596.7 | 1,564.2 | 21,450 | 24,579 |
| 2 | B1 | 115 | 28,844 | 27,461.4 | 5,311.3 | 495.3 | 1,298.3 | 26,163 | 28,760 |
| 3 | C1 | 185 | 28,908 | 27,826.8 | 5,252.0 | 386.1 | 1,005.3 | 26,822 | 28,832 |
| 4 | D1 | 126 | 28,707 | 27,918.2 | 4,588.0 | 408.7 | 1,069.8 | 26,848 | 28,988 |
| 5 | E1 | 109 | 29,076 | 28,099.6 | 4,538.0 | 434.7 | 1,141.4 | 26,958 | 29,241 |
| 6 | F1 | 143 | 28,768 | 27,501.5 | 5,767.2 | 482.3 | 1,259.4 | 26,242 | 28,761 |
| 7 | G1 | 132 | 29,090 | 28,323.5 | 4,528.8 | 394.2 | 1,030.5 | 27,293 | 29,354 |
| 8 | H1 | 110 | 28,721 | 28,222.2 | 3,188.1 | 304.0 | 798.2 | 27,424 | 29,020 |
| 9 | A2 | 144 | 28,790 | 27,638.2 | 5,256.1 | 438.0 | 1,143.8 | 26,494 | 28,782 |
| 10 | B2 | 155 | 28,768 | 28,213.2 | 3,499.0 | 281.0 | 733.3 | 27,480 | 28,946 |
| 11 | C2 | 158 | 28,134 | 27,248.4 | 5,012.0 | 398.7 | 1,040.3 | 26,208 | 28,289 |
| 12 | D2 | 109 | 28,226 | 26,414.6 | 6,549.6 | 627.3 | 1,647.3 | 24,767 | 28,062 |
| 13 | E2 | 111 | 28,544 | 27,788.7 | 4,114.2 | 390.5 | 1,023.6 | 26,765 | 28,812 |
| 14 | F2 | 176 | 28,384 | 28,026.9 | 3,392.1 | 255.7 | 666.1 | 27,361 | 28,693 |
| 15 | G2 | 166 | 27,800 | 26,494.3 | 5,955.0 | 462.2 | 1,204.9 | 25,289 | 27,699 |
| 16 | H2 | 100 | 27,963 | 26,873.3 | 5,251.1 | 525.1 | 1,380.3 | 25,493 | 28,254 |
| 17 | A3 | 127 | 28,497 | 27,705.9 | 4,210.5 | 373.6 | 977.9 | 26,728 | 28,684 |
| 18 | B3 | 114 | 28,476 | 27,065.8 | 5,012.9 | 469.5 | 1,230.7 | 25,835 | 28,296 |
| 19 | C3 | 177 | 27,360 | 25,871.3 | 5,943.5 | 446.7 | 1,163.8 | 24,707 | 27,035 |
| 20 | D3 | 110 | 27,549 | 26,377.3 | 6,197.1 | 590.9 | 1,551.6 | 24,826 | 27,929 |
| 21 | E3 | 118 | 28,690 | 27,960.6 | 3,773.3 | 347.4 | 910.5 | 27,050 | 28,871 |
| 22 | F3 | 136 | 28,290 | 27,650.6 | 3,750.4 | 321.6 | 840.7 | 26,810 | 28,491 |
| 23 | G3 | 149 | 28,602 | 27,360.9 | 5,425.8 | 444.5 | 1,160.8 | 26,200 | 28,522 |
| 24 | H3 | 158 | 28,555 | 27,073.1 | 6,038.8 | 480.4 | 1,253.4 | 25,820 | 28,327 |
| TOTAL | | 3,247 | | 27,255 | 1,116 | 19.6 | 45.6 | 27,210 | 27,301 |

Fig. 9

Definitions:

Sample = the microspheres measured by a single draw from a single well
Population= all of the microspheres in a single well in the 96-well array
Score= the measured bead count and florescence intensity in a single draw
Florescence Intensity Mean (X) = the calculated mean of the measured beads A1= location of single well in 96-well array, designated A1 through H12
C7= bead count (n) for well A1, measured at 119.
E7= intensity mean (X) for well A1, calculated at 23,014.6.
F7= standard deviation(SD) of sample at well A1, calculated at 6,509.5.
G7 =standard error (SE) of sample at well A1, calculated at 596.7,
Level of Confidence in Mean, interval at .01 level = the increment above or
  below the measured sample mean. With a confidence of 99%, the
  sample data supports the conclusion that the population mean is within
  this range. For the measured data, the calculated interval is 1,564.2.
Min Mean= With a confidence of 99%, the population mean is not less than
  the minimum mean calculated. For the measured data, the calculated
  minimum mean is 23,014.6 minus 1,564.2 = 21,450.
Max Mean= With a confidence of 99%, the population mean is not more than
  the maximum mean calculated. For the measured data, the calculated
  maximum mean is 23,014.6 plus 1,564.2 = 24,579.

Calculation Procedures:

Intensity score, x = the measured florescence intensity for each bead
  in the sample.
Intensity Mean, X = total of the individual scores divided by bead count (n)
Standard Deviation, SD = calculated as the square root of
  the sum of the squared deviations from the mean, divided by n-1
Standard Error, SE = calculated as SD divided by the square root of (n)
  =(F7/SQRT (C7))
Level of Confidence Interval = derived from degrees of freedom (n-1),
  the t-distribution value, and the standard error (G7).
  = (lookup (C7-1),C61:D94*(G7))
    wherein C61:D94 is a list of t-distribution values for each value of n-1.

Fig. 10

METHODS FOR ACCURATELY MEASURING ENZYME ACTIVITY

STATEMENT REGARDING FEDERALLY SPONSORED RESEARCH OR DEVELOPMENT

This invention was made with government support awarded by the National Institutes of Health under Funding Agreement Numbers HG003864, CA126764, and CA103235, and NIH EIR number 1413601-09-0005. The government has certain rights in the invention.

FIELD OF THE INVENTION

The present invention relates to the field of biology, relates to improved methods for accurate measurement in laboratory and clinical conditions, and in particular, relates to improved methods for accurate measurement of enzyme activities. More specifically, it relates to a method for the accurate measurement of components in a test sample, such as accurate measurement of activity of enzymes for example, using internal standards.

BACKGROUND

The prior art reflects the continuing challenge to obtain accurate and precise measurements under conditions wherein many experimental conditions are difficult to control. Significantly, the prior art is silent with regard to the influence of random factors on accuracy, statistical significance, and the information content of data used to derive relevant mathematical curves. The methods and protocols presented in relevant technical papers describe a typical embodiment of quantitative analysis that displays wide data dispersion and low correlation coefficients. The prior art highlights an important point that the obstacles to precision become more difficult for test measurements of biological, chemical, and physical functions at the molecular level.

Prior art is described herein on pages 1-3. The failures of prior art are demonstrated by the omissions in prior patents. Prior art recognizes the necessity of constructing a calibration curve (Akhavan-Tafti, 2007, paragraph 0044) and the importance of an internal standard (Chandler 2001, paragraph 0025). However, the methods described result in only an external standard (Chandler 2001, claims 1 through 15) such as daily calibration for machine-to-machine differences (Chandler 2005, paragraph 0129).

The use of even basic internal positive and negative standards for calibration has been shown to improve assay reliability in biochemical experiments using bead arrays (Martins 2002; Hanley 2007). Internal standards are widely used in analytical chromatography, Western blots, quantitative PCR, and quantitative mass spectrometry. The reason for the inclusion of internal standards is that they are especially useful for analyses in which the quantity and quality of sample varies from run to run for reasons that are difficult to control.

For example, gas chromatography/mass spectrometry-based analysis of pollutants demonstrated that internal standards corrected for systematic errors while external standards introduced bias that affected measurement accuracy (Kirchmer 1983). In quantitative polymerase chain reactions (PCR) an internal control gene is used to normalize samples for measures of relative abundance (Livak 2001). Similarly, in quantitative mass spectrometry a control sample is detected simultaneously to provide relative abundance by direct comparison to experimental samples (Ong 2002).

In these cases, quantitation is carried out by a direct ratio of signal obtained from the experimental sample divided by the signal obtained from the control sample. These methods do not define mathematical functions established by statistical parameters that correct for detector response and uncontrollable variables in handling that influence abundance between samples. Indeed, in the case of quantitative mass spectrometry, control samples are prepared and handled independently from experimental samples, thereby excluding them from providing accurate quantitation beyond instrument calibration.

Although internal positive and negative controls have been included in prior art, internal standard curves that define a mathematical function through more than one calibrated internal standard have not been implemented to quantitatively analyze experimental samples. Although prior art includes internal standards, the standards are used to compare detector performance between samples. Thus, the internal standards serve as basic comparisons for detector calibration instead of quantitative tools for sample-specific analyses.

For assays that measure multiple components of a reaction, an additional concern is the normalization of output contributions by various components of the reaction. For example, while multiple peptides are readily detected in a single scan by mass spectrometry, the difference in ionization potential between phosphorylated and un-phosphorylated forms results in over-representation of one species over another (Busman, Schey et al. 1996). Internal standards for one molecular species are irrelevant for the other. Accordingly, only ratios of observed abundance can be obtained to describe relative relationships without statistical significance.

Generally, the prior art does not provide a sufficient number of internal controls to ensure accurate measurements of test samples against calibrated standards. The prior art does not use internal standards to quantitatively analyze the test samples with statistical confidence. Although the prior art uses calibrated standards, the prior art does not force all measurement conditions for the standard and the test sample to be identical. Technical challenges associated with standardizing reagents used in chemical and biological methods result in inherent problems caused by uncontrolled variations between samples and between laboratories.

For example, high-throughput biological screens often note that the organization of samples within plates and small variations between plates can lead to strong sample bias (Koren, Tirosh et al. 2007). Significantly, even basic quantitation in chemistry and biology requires external standards for a combination of background subtraction resulting from non-specific interactions in complex samples, and the calculation of proportions relative to a baseline (Xiaoming, Syuhei et al. 2008).

Although several papers discuss internal controls, the typical methods described depend on external standards and are therefore not sensitive to uncontrollable variables between samples. For many circumstances, an internal standard is only used as a baseline to provide a proportionate measure of abundance for experimental samples. In most cases, the prior art fails to provide a method to simultaneously measure both the control standard and the test sample simultaneously, as an integral part of the test sample. Because prior art necessarily includes inherent variation in test conditions that involve separate controls and test samples, the result is significant inaccuracy. The prior art that does include internal controls uses them as calibration standards and does not allow multiple internal control standards to provide multiple simultaneous comparisons of the test sample versus the control standards or the control standards versus each other.

The following is a discussion of problems with the prior art and the resulting need for a new method that would resolve the important measurement issues.

The Requirement for Accuracy

Extreme precision is required for measurements at the molecular level, such as enzyme activity. Despite the importance of accuracy, the prior art shown in current publications result in high data dispersion and resulting low confidence in the test results, even after selective exclusion of outlier data. As a result, many authors fail to show the statistical confidence intervals in data plots, and typical functional curves exhibit low correlation coefficients. Typically, the resulting wide data dispersion supports only a rough figure of merit (Zhang, Chung et al. 1999).

This invention solves these difficulties by establishment of a standard curve based on multiple data points for each reaction to provide a calibrated standard response. In this way, the previously uncontrolled factors are measured with precision, so that sample data from each test can be meaningfully compared. This novel method uses an internal standard curve for each test and for triplicate groups of tests during an experiment. This method provides a standard for comparison that prevents imprecision caused by subtle but uncontrolled variables. Therefore, this method provides a practical solution to the critical need for high accuracy measurements under conditions wherein many variables are extremely difficult to control.

This novel method is applicable to the broad range of test equipment and procedures for precision measurements required for biochemistry, biophysics, and chemical engineering. By contrast with prior art, the specific protocol described by this novel method results in minimal data dispersion, calculation of the mean with narrow confidence intervals at the 0.01 level, and derivation of precise mathematical curves based on the least-squares fit with an unusually high correlation coefficient. This method establishes calibrated internal controls with statistical relevance to avoid the data dispersion caused by uncontrollable variables.

The Requirement for Comprehensive Internal Standards

By definition, an internal standard must be based on each sample, and measure all relevant variables that could reasonably affect the test. To qualify as an internal standard, the calibrated standard control must be established for the test conditions for each sample. For the accuracy required for measurements at the molecular level, an internal calibration standard must be based on samples drawn from a specific segregated population under controlled test conditions. As a critical flaw, the calibration to external standards has the inherent risk of changed test circumstances due to variables that are very difficult to control.

The methods to develop and apply an internal standard curve for quantitation of individual sample data are unique. Significantly, the internal standard curves provide the basis for reaction-specific quantitation while controlling for detector bias and uncontrollable factors from handling procedures such as non-homogenous distributions. Internal standards are a practical requirement for analyses that exhibit differences in sample quantity and quality for different runs. For many types of test equipment, internal standard curves are rare because most platforms do not allow for the analytical separation of multiple components in the same test sample.

For many types of laboratory tests, internal controls are a practical necessity due to many variables that are difficult to control, such as sample variables or test conditions. For example, establishment of internal standards is necessary for quantitative chromatography and mass spectrometry, where injector and detector performance with small volumes is not reproducible. By contrast, establishment of internal standards remains a challenge for many test methods, such as Western blot, antibody-based studies, and array equipment.

Statistical inference is a practical necessity to establish the accuracy of the test measurements. Definitions of terms used for statistical inference depend on the circumstances under which tests are performed. As applied to array equipment, the population is defined as each reaction in the array from which samples are drawn. The score is the measured signal intensity. The sample is the number of individual units analyzed by a single use of the sampling device. The stratified sample is defined as the combined results of triplicate tests designed to exhibit identical conditions that can be controlled.

Problems Caused by Uncontrolled Variables

It is noted that uncontrolled variables typically cause minor variations in test results. For example, even with the same test equipment, for reactions with the same mixture and tested at the same time, there are variations in the number of samples (n) and the score of each sample (x). Therefore, even minor variations in the sample data may result in major changes in the mean, confidence interval, and mathematical function curve.

A critical requirement for an internal standard curve is that an assay must be able to measure more than one component in a mixture. Although new equipment, including mass spectrometers and high-density matrix arrays, has been developed to measure multiple components of a biochemical reaction, allowing improved test measurements at the molecular level, the test methodology typically results in ambiguous results. This ambiguity is caused by the presence of variables that are difficult to control.

For example, although there are several types of new equipment and reagents that aim to measure enzyme activity, the results of the methods and protocols described in recent technical papers typically display wide data dispersion and a low correlation coefficient, and resulting low confidence in the mathematical functions derived from the ambiguous data. Typical recent scientific papers exhibit data results that are not statistically significant and reflect wide random variation. Generally, an underlying reason for this wide dispersion of test data is test conditions that are difficult to control.

As applied to equipment that samples a given reaction multiple times, the internal standard curve effectively corrects for factors that are not feasible to control between samplings, including but not limited to the number of measurements acquired and variability in the reaction mixture between samplings. Examples of conditions that are difficult to control in a multiplexed bead array include the number of microspheres sampled and analyzed and identical reaction mixtures in each sampled unit.

Current technology allows the measurement of multiple components in a reaction and multiple reactions in an experiment, providing the opportunity for rapid analysis of many samples. Current analytical techniques based on this technology have resulted in a wide dispersion of data that results from conditions that are very difficult to control due to measurements on a very small scale. The invention solves these difficulties by establishment of a standard curve based on a set of known data points in each reaction unit to provide a set of calibrated standards with statistically relevant response. In this way, previously uncontrolled factors are measured with precision, so that results from each component in each reaction can be meaningfully compared.

Discussion of Unresolved Issues with the Prior Art

This method is applied for the accurate measurement of enzyme activity, which is an important issue and essential for future biochemical research. Various enzyme activities are responsible for intracellular signaling cascades that lead to changes in cellular physiology. The post-translational phosphorylation of proteins, considered the most common means of intracellular signal propagation and amplification, is traditionally surveyed by a series of experiments, each querying a single kinase. New technologies have made it possible to measure more than one kinase activity in a single reaction.

Kinases are enzymes that transfer the γ phosphate of adenosine triphosphate (ATP) to tyrosine residues on substrate proteins (Robinson, Wu et al. 2000). Kinases mediate critical growth and survival signaling pathways in response to cell-to-cell contact, peptide hormones, and cell stress. Inappropriately activated kinases play a role in cancer initiation and progression. As such, they are key pharmaceutical targets and research pertaining to their activities involves the investment of hundreds of millions of dollars per year.

As an example of the accuracy issues involved with prior art, the following discussion focuses on a common example of measuring kinase activity to monitor intracellular signaling. The classic approach of measuring kinase activity is to measure the incorporation of radioisotope-labeled phosphate. This method is not easily applied to complex samples with multiple components, such as cell lysates, and cannot be used to measure more than one kinase activity in a single sample.

Several current methods, such as Western blots or microscopic techniques using immunohistochemistry and immunocytochemistry, only infer kinase activity by indexing changes in kinase expressions and phosphorylation states over time. In these cases, the observed signal is a compiled average of the total molecular content in the sample. Triplicate experiments are performed when possible to derive some measure of predictability in the results; however, data are only qualitative and cannot be used to provide statistical inference. With the ability to calculate the average signal per population of cells, flow cytometry provides quantitative measures of phosphorylation events in cells (Perez and Nolan 2002).

However, internal standard curves have not been implemented to increase confidence in measurements. In general, these methods are heavily dependent on existing protein-specific antibodies and detection is focused on a single reagent, for example the phosphorylation state of a particular kinase. Therefore, these methods have a limited capacity for measuring multiple components in a single reaction. In principle, a phospho-specific antibody could be matched to each substrate and detected independently in solution, but this creates significant challenges. The development of internal standards by extension of this strategy is challenging but can be done.

A critical requirement for the embodiment of the invention is that multiple components of a reaction must be monitored simultaneously. To monitor multiple components in a reaction, methods have been developed that provide unique tags to capture multiple substrates from a solution-phase reaction (Shults, Kozlov et al. 2007). Kinase assays are also performed with peptide and protein substrates tethered to surfaces (Henderson and Bradley 2007). For example, peptide microarrays offer detection of multiple substrates with spatial addressing. These formats allow the interrogation of multiple kinase activities in cell extracts with the detection of a single generalized label, such as a fluorescent anti-phosphotyrosine antibody (Houseman, Huh et al. 2002). This chip-based approach can also be adapted to a multi-well format (Wu, Mand et al. 2008).

An alternative format for monitoring multiple components in a reaction is the use of bead arrays. Bead arrays can be used to monitor the phosphorylation of multiple endogenous substrates in cell lysates by immobilizing a different capture antibody on different types of beads and detecting phosphorylation with a second phospho-specific antibody (Du, Bernasconi et al. 2009). Kinase activity assays are readily implemented using kinase substrates immobilized on beads (Wu, Nair-Gill et al. 2005). It is therefore straightforward to design activity assays using beads to simultaneously monitor more than one component of a reaction (Bernsteel, Roman et al. 2008). Although the use of beads in an assay allows sample counting and population-based statistics, these principles have not been previously implemented to increase measurement accuracy and confidence.

The solution to the problem of assigning statistical significance to data that displays high variability is to increase the number of replicate samples analyzed. Generally, prior art is limited to the analysis of experiments performed in triplicate. Data are sorted by qualitative comparisons and outliers are removed without explanation. The results may or may not be predictive of future attempts and statistical validation is not available to provide a measure of confidence. The present invention solves this issue by providing quantitative internal standard curves for each reaction performed in triplicate. Therefore, the invention allows for each of the triplicate test samples to be (a) simultaneously measured, (b) identical as to all known controllable conditions, and (c) include the calibrated control standard within each sample.

For practical application, the issue is whether this method provides additional information that cannot be acquired through other means. Several companies have produced equipment designed to allow high-throughput assays of kinase phosphorylation, including Luminex, Cell Signaling Technologies, Kinexus Bioinformatics Corp., and Qiagen. Established sources can supply control beads for testing bead I.D. and reporter I.D; however, these controls only validate the working condition of the instrument and do not provide an analytical tool for experimental tests. Although there is a wide range of specialized equipment and activity assay formats, accurate measurement of kinase activity has remained a persistent challenge. The use of internal standard curves for experimental quantitation and statistical validation significantly improves the reliability of sample comparisons.

SUMMARY

The invention is a novel procedure for use with test equipment that substantially increases the accuracy and reliability of the equipment measurements. The test equipment includes, but is not limited to, machines that utilize multiplexed arrays, mass spectrometry, liquid chromatography, or other chemical and biochemical devices typically used in a laboratory or clinical setting. The novel procedure is a method to utilize the specialized equipment in a unique way, so that a control is established as a foundation for comparison.

The control data is based on precision measurement and statistical inference for the unique characteristics of each individual reaction or sample group. This measurement method prevents errors based on variation that is not feasible to control in test samples. This measurement method allows accurate measurements at the molecular level, under conditions wherein uncontrolled random differences may produce data scatter that prevent accurate measurement.

For both the control data and the comparison test data, the subject matter to be tested is divided into separate reaction vessels that are intended to be identical, excepting only one controlled variable. Significantly, each reaction typically has random differences that cannot be controlled with existing technology. Then, samples are taken from each reaction, under various conditions ranging from a baseline condition to an extreme test condition. For each reaction and each condition, there is a physical count of the number of samples (n), and a measurement of the attained score for each sample in each group (x). From this data, statistical inference methods, with modification for the specific sample size (t-distribution), provides the mean and the confidence interval for the mean.

Control of Random Variations

The random differences between nominally identical reactions are controlled through an additional step. The nominally identical reactions are grouped into a strata, with separately calculated statistical results. Because this detailed data is provided for each sample, each reaction, and each strata, the random differences are controlled because the variations between nominally identical reactions are measured.

Terminology varies with the specific equipment. For example, for multiplexed bead arrays, a reaction vessel is defined as one of the wells in a 96-well array, a score (x) is the measured florescence at the surface of each microsphere, the mean is calculated based on attained scores for each microsphere in a specific well, and the confidence interval is calculated from the mean and the deviation from the mean. Then, the strata are defined as groups of three nominally identical wells per controlled variable.

Calibrated Standard for Each Experimental Sample

As applied to the measurement of kinase activities, the principle and distinct feature of the invention is to add a set of four internal standards to each experimental sample prior to antibody labeling for the accurate measure of kinase activity. The internal standard curves are generated by at least four points per well of a known percentage of substrate phosphorylation; these curves are used to translate the fluorescence readout from bound anti-phosphotyrosine antibody to a meaningful scale. Standard curve-based calculation of well-to-well variations in antibody binding allows for the measurement and validation of small changes in substrate phosphorylation by un-fractionated cell lysates as well as purified recombinant enzymes.

The accuracy of each measurement ensures that the assay is sensitive enough to be used with very small amounts of cell lysates and/or concentrations of additional reagents, including ATP. As a functional assay, examples of this method are limited by the endogenous activity of the enzyme of interest and the specificity of the tested substrate for that enzyme. The prior test methods typically result in wide data dispersion, which has resulted in the adoption of selective editing of outlier data points and non-dimensional figures of merit. By contrast, this method establishes a calibrated internal standard curve for each test sample, which effectively controls the previously uncontrollable variables, and results in highly accurate test results, with a precise fit to standard mathematical functions and a narrow confidence interval at the 0.01 level of significance.

Advantages of the New Method

By contrast with prior art, the specific protocol described by this novel method results in minimal data dispersion, calculation of the mean with narrow confidence intervals at the 0.01 level, and derivation of precise mathematical curves based on the least-squares fit with an unusually high correlation coefficient. It has been demonstrated that this method provides a high level of accuracy and resulting confidence in the test results. This method of establishment of calibrated internal controls to avoid uncontrollable variables is expected to be applicable to a wide variety of test conditions that require extreme precision and high confidence in the results.

The method measures both the control and the test variable simultaneously under identical conditions. Importantly, calibrated reference points and experimental samples are processed in a single test run so that random and intentional conditions affect all measured values identically. Therefore, the broad range of variables which are difficult to control are integrated into the calibrated standards, so that the measured results for the test condition are caused by the changed circumstances instead of the uncontrolled variables.

Using internal standards, samples can be monitored with sufficient sensitivity to allow accurate measurements using very small amounts of test material. As a typical embodiment, the method is applied to the measurement of enzyme activity for the functional analysis of biological signaling events and the identification of effective inhibitors for the treatment of disease; however, the method can be applied to any chemical or physically modifying reaction and may be useful in the establishment of industrial processes.

Due to the precision of measurements using internal controls, the test data exhibit very narrow confidence intervals and unusually precise fit to the derived mathematical curves. By contrast, as shown by many recent publications of tests of protein functions, prior art typically results in a wide data scatter with inherent high risk of error. This novel method offers unique and valuable advantages over prior art, based on the demonstrated high accuracy. With this method, the broad range of variables which are difficult to control are integrated into the calibrated standard controls, so that the measured results for the test condition are effectively segregated from the uncontrollable variables.

This novel method provides the foundation for prompt, accurate measurements that are necessary for high-throughput and clinical assays, including enzyme inhibitor screens and diagnostic testing. For example, this method is useful for accurate assays of kinase activity as measured by substrate phosphorylation and derived from small changes in bound antibody fluorescence over time in a large array of samples. Typical applications include, but are not limited to, the analysis of cellular signaling pathways and assessment of the effectiveness of pharmaceutical inhibitors.

Accordingly, this novel method has potential for wide applications to address biochemical issues that require accurate measurement for reliable comparisons, combined with high throughput. Included in the method is custom software that allows for the accurate calculation of confidence intervals for the specific sample size for each unit, using widely accepted statistical inference criteria. A typical embodiment of this method would include equipment that allows multiple components of a sample to be measured simultaneously. The method is applicable to several types of laboratory and clinical equipment, such as but not limited to, bead arrays, chip arrays, mass spectrometry, and liquid chromatography.

BRIEF DESCRIPTION OF THE DRAWINGS

In FIG. 5A, synthetic standards with increasing phosphorylation were arranged in separate wells, as in traditional calibration curves. In FIG. 5B, standards constructed from three different forms of background signal were compared to estimate the variance in non-specific detection. For both cases, standards were arranged in a 96-well plate, labeled with fluorescent anti-phosphotyrosine antibody, and the detector was run three consecutive times on standard laboratory equipment (Bio-Plex 200, BioRad). The only change to the plate between runs was the added Luminex running buffer from the Bio-Plex 200 upon replacement of the sampled beads. Triplicate columns are grouped to show separate measurements for runs 1, 2, and 3 per well, for triplicate wells, in arbitrary units of raw fluorescence intensity. While some wells had consistent values across three runs, others showed large variability from run to run. Error bars represent the 99% confidence interval around the mean and are a function of the number of beads sampled per run. This variability between runs and between wells undermines the effectiveness of an external standard but does not affect the validity of an internal standard. This data strongly support well-specific internal standards for accurate measurements that are independent of plate-to-plate and run-to-run fluctuations.

FIG. 6A shows the calculation of the mean for 7 data points, showing the confidence interval (CI) at the 0.01 level, which is a 99% probability that the results are not due to random variables. The mathematical curve shows the correlation coefficient ($R^2$) of 0.98, which shows a very high confidence that the curve describes the underlying test data. Replicates of the same well were not required because measurement confidence can be derived from each sample. FIG. 6B shows the effect of lapse of time on the percentage of substrate phosphorylation by kinase in cell lysates. Data were transformed through internal standard curves from raw fluorescence intensity to the accurate percentage of phosphorylation, and fit to a saturating hyperbolic curve with a very high correlation coefficient of 0.94 to show the accuracy of the underlying data. This method allows a mathematical analysis of the data to confirm enzyme activity with high confidence based on a single objective experiment.

FIG. 8A illustrates the raw data from a typical embodiment using three distinct peptide substrates, Abltide, Srctide, and a peptide derived from Btk, immobilized on Luminex beads and treated with dilutions of the inhibitors imatinib (μM range, at the right) and dasatinib (nM range, at the left). Results for multiple substrates detected from the same reaction mixture are analyzed with 99% statistical confidence about the mean. Each curve is self-normalized with a minimum at 0 and maximum at 1, to facilitate visual comparisons between substrates with absolute values that differ by up to 100-fold. FIG. 8B demonstrates the effect of using internal standard curves to transform each data point according to well-specific parameters established by the calibrated control standards. The phosphorylation of each substrate is related to the internal standards by a Boltzmann-sigmoidal curve that defines the system response. The sigmoidal inhibitory curves demonstrate altered slopes when defined in relation to the internal calibrated standards. This highlights accurate relative differences between components in a single reaction. This figure shows that the test method allows sufficient accuracy for a detailed comparison of multiple variables in a single test.

FIG. 9 presents a selection of data organized by the custom software included in the invention and used to analyze results from a typical embodiment for statistical significance. In this selection an internal calibrated standard for 50% phosphorylation is described in 24 wells of an array. In each well, the number of beads sampled and the median, mean and standard deviation of the signal are reported by the standard laboratory equipment. For each sample, the standard error and 99% confidence interval is calculated based on the standard error (SE), which is calculated from the sample size (n), mean intensity (X), and the standard deviation (SD), which are the basic outputs from typical equipment. The custom software performs the critical calculations to establish the statistical significance of the measured data. This calculation is performed for each component of a reaction, including each calibrated standard so that the statistical significance is described for each and every measurement. A preferred embodiment of this software is shown in the spreadsheet submitted herewith.

FIG. 10 is a description of the specific calculation procedure provided by the custom software that results in the accurate calculation of the standard error (SE). This figure shows the specific keystrokes within Excel (Microsoft Office, 2008) that comprise the critical calculations. Standard statistical software based on a normal distribution is not used, because the small sample size requires the t-distribution. Within Excel, the t-distribution values are arranged in a detailed lookup table. Thus, this spreadsheet results in an accurate calculation of the statistical significance of each measurement Details of this spreadsheet are submitted herewith.

DETAILED DESCRIPTION

Figure 1:
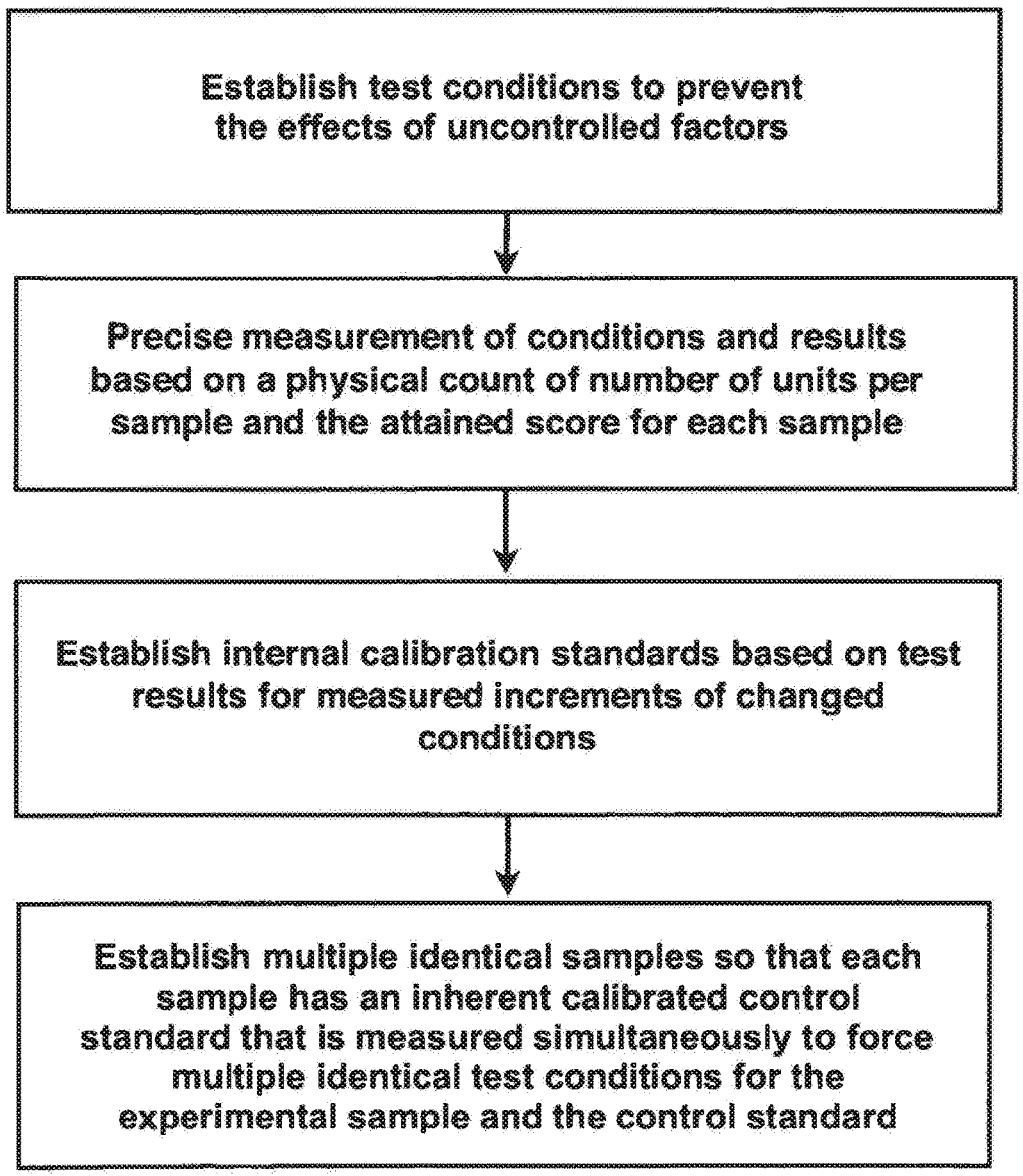
FIG. 1 is a summary of the primary elements of the test procedure. This figure describes the essential features for the establishment of test conditions that offset the effects of uncontrolled factors. This is done by precise physical measurement including a physical count of the number of units per sample. The internal calibration standards are established based on test data from the same test equipment and the same test mixture.
Figure 2:
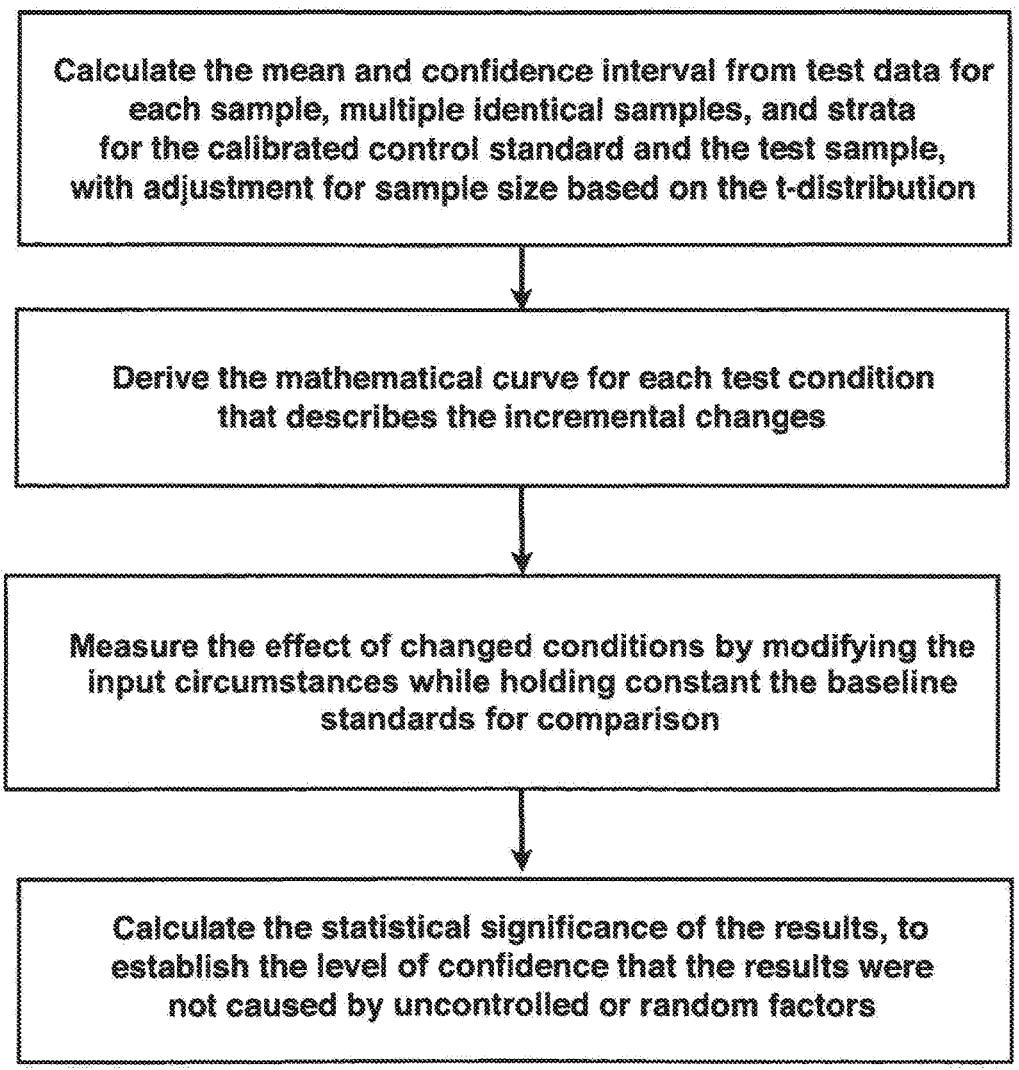
FIG. 2 is a summary of the primary elements of the method, with emphasis on accurate measurement and the use of statistical inference to provide confidence in the results. Because the test method results in minimal scattering for the data points, the mathematical curve that describes the functional effects exhibits a high correlation coefficient. Mathematical curves are established for each test condition to serve as the calibrated control standards.
Figure 3:
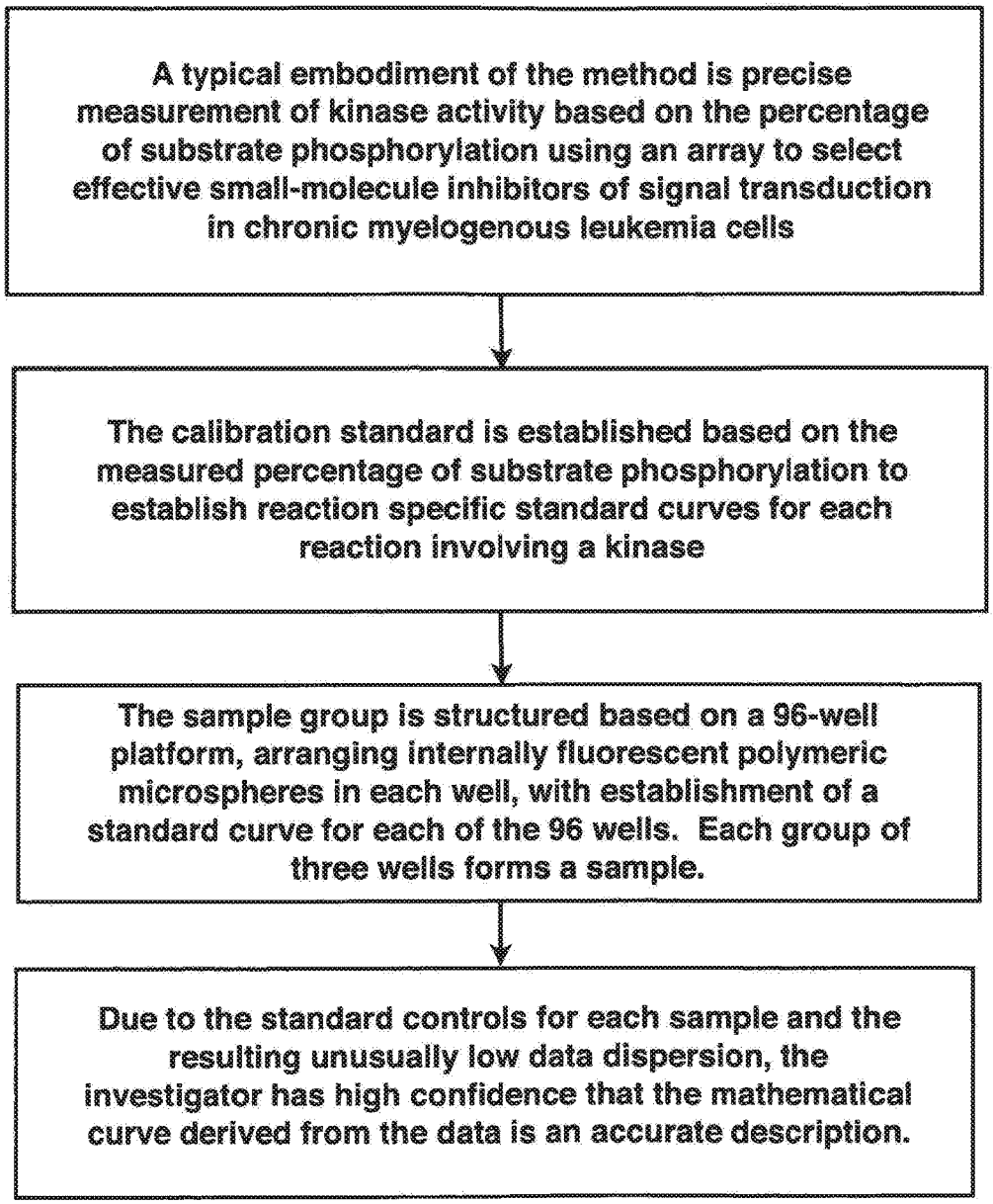
FIG. 3 is a summary of the typical embodiment of the method for measurement of kinase activity using equipment that can simultaneously monitor more than one component of a reaction. A standard curve is derived for each reaction in each well in a 96-well array. Peptide substrates are covalently immobilized on specialized beads that can be analyzed in distinct populations. The test sample is compared to an internal standard curve constructed from synthetically phosphorylated peptide substrates.
Figure 4:
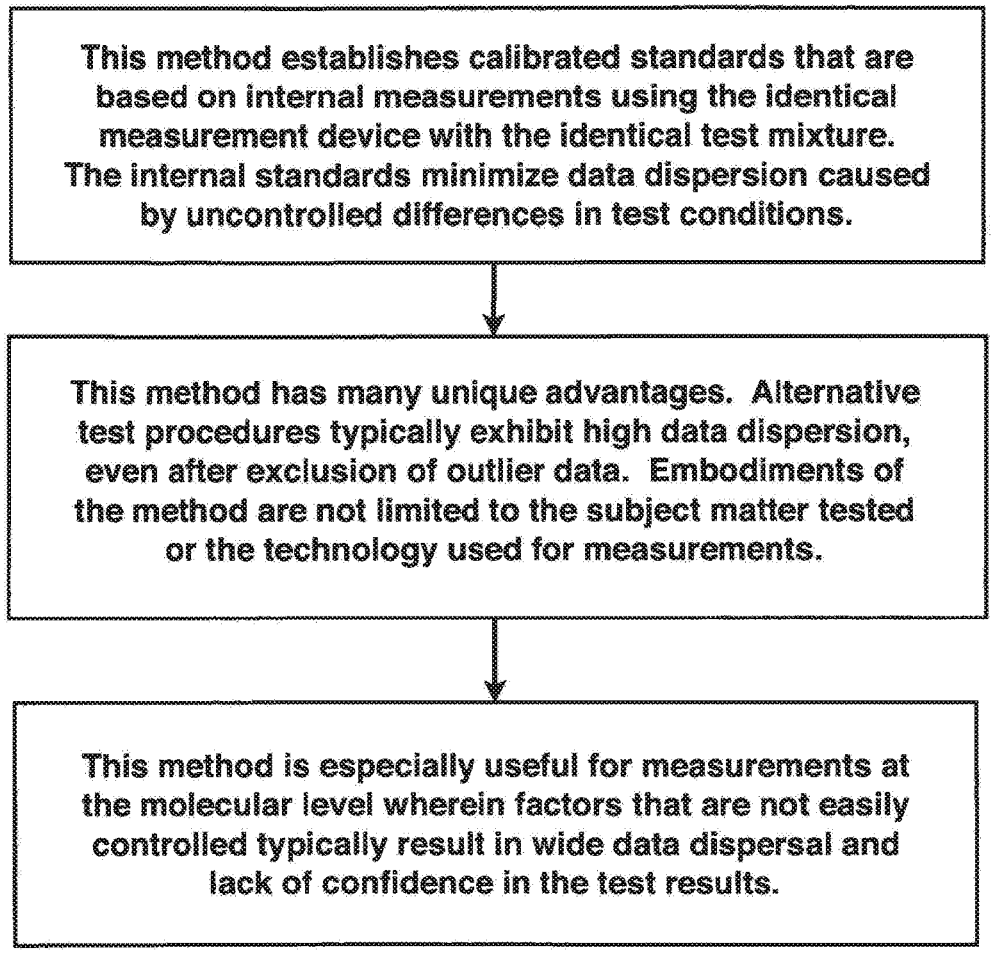
FIG. 4 summaries the essential characteristics of the internal standard curve in a typical embodiment. For array-based embodiments, the standard curve describes each reaction in an array. In a typical embodiment, standards are added to each well after termination of the kinase reaction and before labeling the phosphorylated substrate with fluorescent antibodies. The internal standard curve corrects for differences in antibody binding and uncontrollable reaction conditions between wells.
Figure 5A:
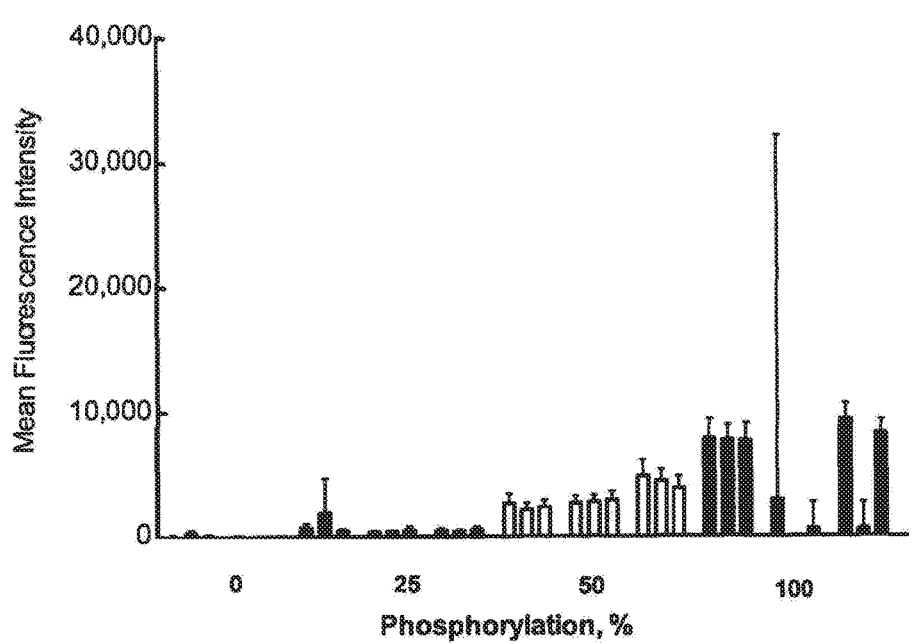
FIG. 5A and FIG. 5B demonstrate that for typical biochemical equipment replicate wells and replicate runs of the same well result in variability and scattered data distributions with low confidence.
Figure 5B:
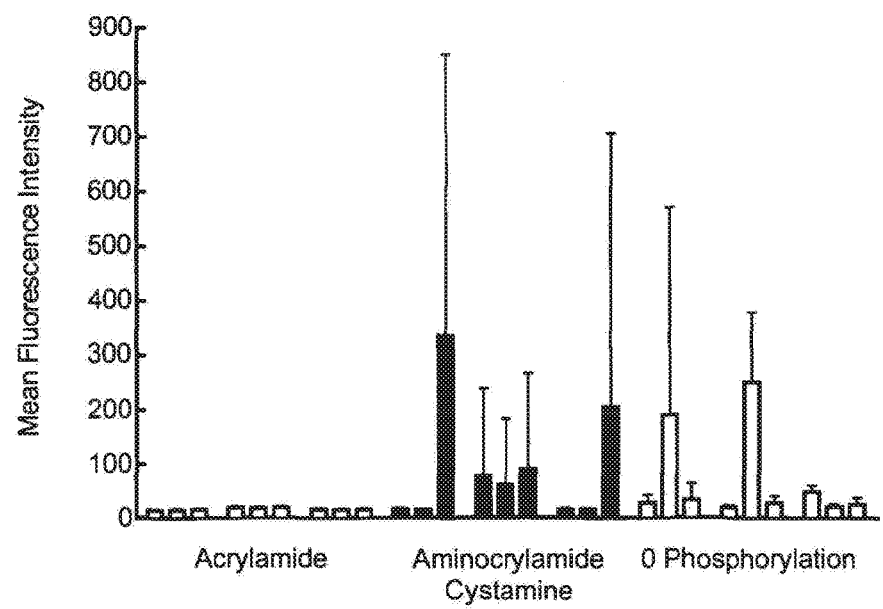
Figure 6A:
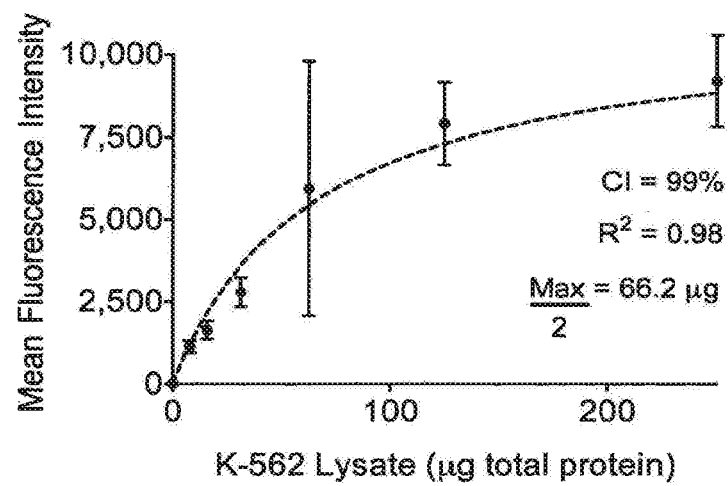
FIG. 6A and FIG. 6B show the preferred embodiment of test data.
Figure 6B:
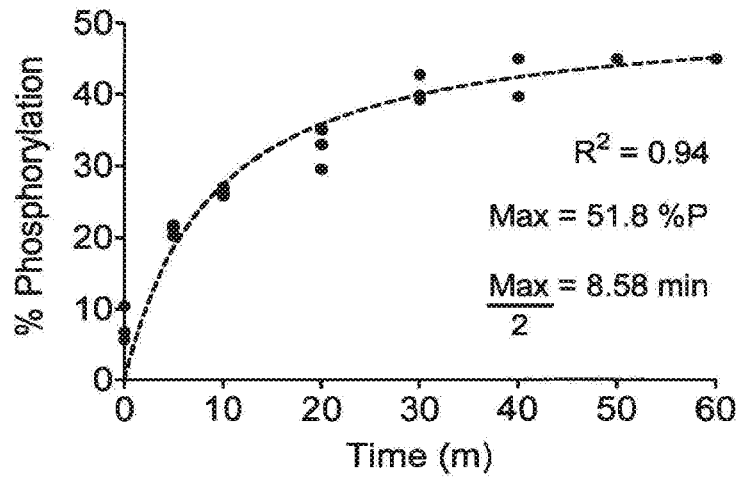
Figure 7:
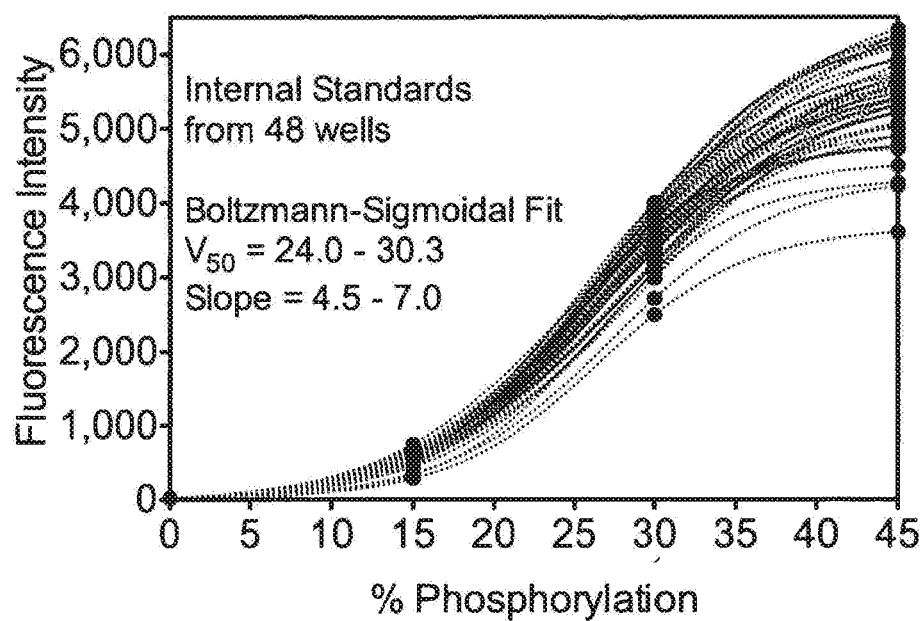
FIG. 7 is a plot of the unique standard curve for each of 48 wells in an array. The plot shows the relationship of fluorescence intensity to the percentage of substrate phosphorylation. For each well, the Boltzmann-Sigmoidal curve provides a very good fit, emphasizing a concentration-based dose response. Significantly, the variability between internal standard curves in each well highlights the weaknesses of prior methods, which use only one external standard curve per plate or per day.
Figure 8A:
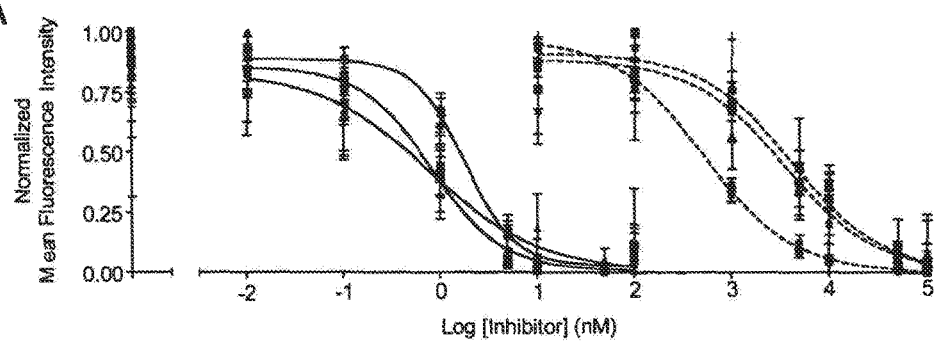
FIG. 8A and FIG. 8B show the low data dispersion and resulting accurate calculation of the mathematical function curves based on test data derived using the novel test procedure, based on internal calibration standards.
Figure 8B:
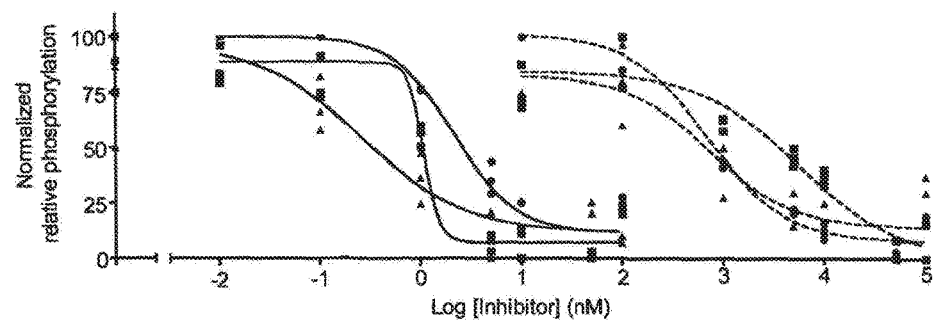

The following provides a description of the present invention, a typical application of the method including the procedure for establishment of the calibrated internal standard curves, and an example of results of the test procedure. The application described utilizes groups of microspheres arranged in a 96-well plate to facilitate parallel measurements on the effect of different kinase inhibitors used in the treatment of leukemia.

The aim is to improve the resolution of diagnostic tests for chronic myelogenous leukemia (CML) by providing more than one marker of patient progress. To achieve statistical significance for accurate sample comparisons, we developed an embodiment of the invention that used a platform of internally fluorescent microspheres (acquired from the Luminex corporation) for simultaneous measurements of experimental and control parameters to monitor kinase reactions in human cell lysates.

Bead array analysis, implemented using the Luminex platform of internally-fluorescent polymeric microspheres, offers an ideal format for monitoring multiple analytes in a single sample (Fulton, McDade et al. 1997). The platform uses a dedicated flow cytometer to track up to 100 components per reaction in each well, while processing multiple conditions in 96-well plates. This is accomplished by a pair of lasers, one to excite internal red fluorescence for bead identification and count and the second to excite green fluorescence at the bead surface to measure analyte levels.

The platform allowed for high throughput and quantitative analysis of multiple kinase activities in a single experiment, using internal standard curves to accurately compare samples. This embodiment of the invention, which uses an internal standard curve to accurately measure systematic and intentional changes, provided a quantitative assay for profiling tyrosine kinase activity in a biological context. Usefulness of the invention is demonstrated by unusually high accuracy measurements of multiple tyrosine kinase activities in cell lysates from a single well of a 96-well plate, using standard laboratory equipment.

The embodiment focuses on tyrosine kinases and directly calculates the percentage of substrate phosphorylation via non-linear regression from internal standard curves. The synthetic kinase substrates Abltide, Srctide and a peptide derived from Btk are immobilized on Luminex beads to facilitate handling procedures and enable the analysis of more than one component per reaction. Fluorescent antibodies are used to label substrate phosphorylation sites.

Antibody fluorescence intensity is translated directly to enzyme phosphotransferase activity through internal standards included in each well of a 96-well plate. Serially diluted inhibitors are applied to different wells of a 96-well plate to measure the effect of variable inhibitor concentrations on kinase activity. Because of the precise quality control implemented through internal standards, the test data exhibit an extremely low probability of error, with statistical significance at the 0.01 level.

The subject invention demonstrates substantially improved information content with a measurement scale that provides equal intervals for improved precision. As a result, data are analyzed by statistical correlations to calibrated standards and not merely ordered by rank. The measurement accuracy allows for standard methods of statistical inference, such as the t-test for level of confidence. By contrast, external standards are generally used for assays based on the Luminex technology and lack individual calibration for any well.

Typically, arrayed data fail to meet the standards required for standard statistical methods. This lack of an established baseline results in information content that is limited to rank order sorting, with insufficient information content in individual reactions to allow calculation of the mean, the standard deviation, and resulting levels of confidence. With an external standard and resulting accuracy limited to ordinal measurement, the information content is limited to the use of a dimensionless figure of merit, such as the Z' value, or alternative standards. Although measurement precision is not feasible for some situations, and alternative protocols have been developed to allow reasoned decisions based on limited information content, improved precision is widely recognized as the preferred foundation for test results.

The application of the invention is this embodiment defines the first reported use of well-specific internal standard curves to calculate the accurate percentage of substrate phosphorylation following reactions with kinases in cell lysates. The invention has been used to reliably measure the simultaneous phosphorylation of Abltide, Srctide and the peptide derived from Btk for an in-depth view of intracellular network dynamics during treatment with clinically relevant inhibitors. With high-throughput formatting and requiring only hours for completion, this assay is expected to be a valuable tool in clinical settings.

This embodiment improves the resolution of diagnostic tests by providing statistical relevance to observed differences and sample comparisons. The benefits of the invention are demonstrated by an embodiment that can be routinely used for quantitative, high-throughput screening of kinase inhibitors and is easily be applicable in the clinic to assess CML patients undergoing treatment.

EXAMPLES

The following is a non-limiting example of a typical practical application of the invention for measurement of enzyme activity by the quantitative phosphorylation of peptide substrates. Expanded application of the novel method would allow parallel applications for circumstances that require accurate quantitative analysis and assay robustness, such as diagnostic testing of patient samples, modeled here using a human cell line for chronic myelogenous leukemia, and pharmaceutical screens using a small set of clinically-relevant inhibitors. Persons familiar with the art would be aware of useful application of this basic method with other laboratory equipment, test conditions, or test samples.

The method results in a quantitatively robust assay for the functional analysis of intracellular signaling events, based on a covalently immobilized set of synthetic peptide substrates on fluorescent Luminex beads. Phosphorylation of the peptide substrates by active kinases present in cell lysates is detected by a phycoerythrin-labeled anti-phosphotyrosine antibody.

The Luminex system uses two orthogonal lasers to display both internal bead fluorescence, which identifies the bead region and counts the number of beads analyzed, and phycoerythrin fluorescence at the bead surface, bound by interaction with the phosphorylated substrate. Only phycoerythrin that is bound to a bead surface is recorded. Results from Luminex assays are typically displayed as the median fluorescence intensity, in arbitrary units, per a minimum of 100 beads. This method reports the mean fluorescent intensity of the total number of beads counted to allow statistical analysis of the population results, providing robust 99% confidence intervals for each sample.

Substrate Immobilization on Luminex Beads

To measure the characteristic Bcr-Abl activity profile of CML, the standard high-affinity peptide substrate for c-Abl and its oncogenic relative Bcr-Abl (CEAIYAAPFAKKK) is synthesized. The established core recognition sequence was modified only by the inclusion of an amino-terminal cysteine, for specific covalent attachment to Luminex beads.

To enable separation of the substrate from the reaction components, the synthetic peptide on Luminex beads is immobilized. Luminex beads are supplied in bulk with free carboxyl groups and can be modified with primary amines using standard methods. To provide distance between the bead surface and the site of phosphorylation on the peptide substrate, a biologically passivating N-(3-Aminopropyl) methacrylamide linker was introduced using EDC/NHS crosslinking.

Abltide peptide substrate was covalently attached to the bead surface by Michael addition of the sulfhydryl at its amino-terminal cysteine to on-bead acryl groups. All conjugation steps were carried out in filtered microcentrifuge tubes to enable easy removal of excess reagents and wash steps. Modified beads were counted using a hemacytometer and stored refrigerated for up to a year in phosphate-buffered saline, pH 7.4.

Substrate Phosphorylation by Cell Lysates

The K-562 cell line was established from a CML patient in terminal blast crisis and is characterized by highly undifferentiated cells of the granulocytic series. With a low frequency of the Philadelphia chromosome but highly upregulated Abl kinase, the K-562 line serves as an ideal model for testing CML diagnostics. Kinase assays were performed in 96-well filter plates to accommodate high throughput processing. A liquid handling robot was used to efficiently transfer approximately 1000 beads to each well of a 96-well filter plate. A 50 μL/well reaction mixture, containing kinase buffer (50 mM Tris-HCl pH 7.5, 10 mM MgCl2, 1 mM EGTA, 0.01% Brij-35, 2 mM DTT, Complete protease inhibitor cocktail), 10 μM ATP and variable concentrations of purified enzyme or cell lysates, were incubated with the beads for up to one hour.

The kinase reaction was terminated by the addition of 250 mM EDTA, pH 8.0, which chelates the cofactor $MgCl_2$ that is required for Bcr-Abl activity. A brief wash with 2% SDS was used to remove non-specific adsorption of cellular proteins and 1% BSA was used to block nonspecific binding of labeling antibodies to un-phosphorylated peptides and the polystyrene bead surface. Phosphorylated substrate was labeled sequentially with biotinylated 4G-10, an anti-phosphotyrosine antibody, and phycoerythrin-coupled streptavidin. After phospho-specific labeling the beads are given an optional final wash and re-suspended in the Luminex system running buffer.

The Luminex system removes 50 μL of the suspension and queries a random sample of at least 100 beads out of the estimated total 1000 beads per well. Peptide-modified Luminex beads are phosphorylated by purified c-Abl kinase or by kinases in K-562 lysates, resulting in a change in phycoerythrin fluorescence from x to y in one hour at 30 degrees Celsius. Experiments are performed in triplicate wells. Unmodified carboxyl-coated Luminex beads typically display a background fluorescence of 4 units.

Generation of Internal Standard Curves and Measure of Bcr-Abl Activity

The standards are produced by mixing synthetic Abltide (CEAIYAAPFAKKK) and synthetic phospho-Abltide (CEAI-pY-AAPFAKKK) in known molar ratios and immobilizing those peptide mixtures on Luminex beads. In order to ensure accurate relative concentrations, purified peptides were analyzed separately by absorbance of the peptide backbone at 214 nm with analytical reverse-phase high-performance liquid chromatography (RP-HPLC). The integrated peak areas were plotted versus injection volume per peptide and the ratio of the slopes was used as the calibration factor for relative peptide concentration.

The points at 0% and 100% substrate phosphorylation are generated from pure synthetic Abltide and synthetic phospho-Abltide, while the points at 25% and 50% are produced by corresponding molar ratios of phospho-Abltide to Abltide. Pure peptides and peptide mixtures were covalently conjugated to region-specific Luminex beads by carbodiimide chemistry. Four distinct bead regions, modified with standard phosphorylated peptides, were added to each well of a 96-well plate after the kinase reactions were quenched and the experimentally phosphorylated beads were washed with 2% SDS. All five bead regions were blocked with 1% BSA prior to anti-phosphotyrosine antibody labeling.

The fluorescence readout from the well-specific internal standard curves over an entire 96-well plate is not linear with increasing phosphorylation. The slope and shape of the functional relationship between percent phosphorylation and observed florescence intensity is based on the test data and the calculation of the means and confidence intervals for each cell, and for the entire group of 96 cells. The sample size is the bead count for each well, which ranged from 171 to 668, with a mean sample size of 326. The extent of experimentally phosphorylated substrate is calculated by non-linear regression from the internal standard curve.

The following is a description of the basic materials, equipment, and test procedure that are a practical necessity to assure accurate measurements for kinase activity.

Materials and Reagents

Reagents for peptide synthesis were purchased from Peptides International (Louisville, Ky.). K-562 cells were obtained from American Type Culture Collection (Manassas, Va.). RPMI-1640 media, L-glutamine, and the Kaiser test kit were purchased from Sigma-Aldrich (St. Louis, Mo.). FBS was purchased from Gemini Bio-products (West Sacramento, Calif.). Phosphosafe Extraction Reagent was purchased from Novagen EMD Biosciences (Madison, Wis.) and Complete protease inhibitor cocktail was purchased from Roche Diagnostics (Mannheim, Germany).

The Coomassie (Bradford) protein assay kit, HALT protease inhibitor, NHS, and EDC were purchased from Pierce (Rockford, Ill.). Imatinib and dasatinib were purchased from LC Laboratories (Woburn, Mass.). Purified recombinant human Abl kinase (EC 2.7.10.2), biotin-conjugated anti-phosphotyrosine clone 4G10, phycoerythrin-conjugated streptavidin, and 0.22 µm-filtered microcentrifuge tubes were purchased from Millipore (Billerica, Mass.). N-(3-Aminopropyl)methacrylamide was purchased from Polysciences (Warrington, Pa.). Luminex (Austen, Tex.) generously provided Luminex beads with free carboxyl groups, in bead regions 27, 34, 42, 45, 56, 61, 65, and 73.

Instrumentation

Peptides were synthesized on a Prelude™ parallel peptide synthesizer from Protein Technologies (Tucson, Ariz.), purified on a Waters 6000S HPLC system (Milford, Mass.), and analyzed by MALDI-TOF (4700 Voyager, Applied Biosystems). Modified Luminex beads were distributed to filter plates using a Precision Microplate Pipetting System purchased from BioTek (Winooski, Vt.). Data were acquired with a minimum target of 100 bead counts per region per well using the BioPlex 200 system from BioRad (Hercules, Calif.), calibrated separately at both high (15993) and low (3515) targets to determine the maximum range of detector linearity per plate.

Cell Culture and Lysis

K-562 cells were cultured at 37° C. and 5% $CO_2$ in RPMI-1640 media with 4 mM L-glutamine and 10% FBS (v/v). Lysates were prepared from confluent cells using Phosphosafe Extraction Reagent with Complete protease inhibitor cocktail and tested for total protein content by Bradford analysis.

Peptide Synthesis and Substrate Sequences.

Peptides were synthesized at the 40 µmol scale using a 5-fold excess of Fmoc amino acids (200 µmol per coupling) relative to Rink-Amide-CLEAR resin (87 mg at 0.47 mmol/g). Fmoc protecting groups were removed with 20% piperidine in DMF for 20 m. After 6 washes amino acids were coupled using 1:1:2 amino acid/HCTU/NMM in DMF for 30-45 m. Phosphotyrosine was coupled in HBTU/HoBt/DIPEA for 2 h, and complete coupling was confirmed by the Kaiser test. Both the amino acid N-terminal to phosphotyrosine and the final amino-terminal cysteine were coupled twice for 45 m each. Peptides were cleaved from the resin with 94.5:2:2:1.5 TFA/water/EDT/TIS for 3 h, precipitated with diethyl ether, re-suspended in 5% $CH_3CN$ and lyophilized. Crude peptides were purified by HPLC using a preparative 10×250 mm 10 µm $^{18}C$ column. Both crude and purified peptides were analyzed by MALDI-TOF in linear positive and negative modes using a 1:1 (v/v) mixture of 10 mg/mL CHCA matrix in 75% $CH_3CN$ with 0.1% TFA.

Established kinase substrate recognition sequences were modified by the inclusion of an amino-terminal cysteine for specific covalent attachment to Luminex beads. While Abltide (CEAIYAAPFAKKK) (Songyang, Carraway et al. 1995) and Srctide (CAEEEIYGEFEAKKKK) (Songyang, Carraway et al. 1995) are optimized synthetic substrates, the peptide substrate for Btk kinase was derived from its tyrosine auto-phosphorylation site (CKKVVALYDYMPMN) (Bence, Ma et al. 1997; Yamadori, Baba et al. 1999).

Generation of Internal Standards

Internal standards were generated from synthetic Abltide and phospho-Abltide (CEAI-pY-AAPFAKKK). To ensure accurate relative concentrations between Abltide and phospho-Abltide for 15%, 25%, 30%, 45%, and 50% molar mixtures, purified synthetic peptides were analyzed separately by absorbance of the peptide backbone at 214 nm with analytical $C_{18}$ RP-HPLC. Integrated peak areas were plotted versus injection volumes per peptide and the ratio of the slopes was used as the calibration factor for relative peptide concentration. Pure Abltide and phospho-Abltide were used for 0% and 100% phospho-standards.

Covalent Substrate Immobilization

Luminex beads were modified with primary amines using standard methods. Up to 300 µL of carboxylated beads, supplied at $1.25 \times 10^7$ beads/mL, were added to a filtered microcentrifuge tube, washed with water by centrifugation at 100 g, and re-suspended in 100 mM $NaH_2PO_4$, pH 6.2. 50 µL of 50 mg/mL NHS in water and 50 µL of 50 mg/mL EDC in water were added and the beads were incubated at room temperature for 20 m with gentle shaking (Giavedoni 2005). The beads were washed three times with 100 mM MES, pH 5.0, and re-suspended in 100 µM N-(3-Aminopropyl)methacrylamide in the same buffer. The primary coupling reaction was mixed for 2 h at room temperature. Beads were washed three times with 100 mM $NH_4HCO_3$, pH 8.0, and re-suspended in 100 µM peptide in the same buffer. The secondary coupling reaction was mixed for 1 h at room temperature and allowed to incubate 12-18 h at 4° C. Modified beads were counted using a hemacytometer and stored at 4° C. for up to a year in PBS, pH 7.4, supplemented with phosphatase inhibitor as necessary.

Kinase Assays

Peptide-conjugated beads were diluted to $1.25 \times 10^6$ beads per mL in 10 mM Tris-HCl, pH 7.4 and each bead region was distributed into one row of a black, conical bottom 96-well plate. Using a pipetting robot, 5 µL from each well per row were distributed to each of the 12 rows of a 96-well filter plate. The 96-well filter plate, containing approximately 1000 peptide-modified beads per region per well, was vacuum-washed three times with 10 mM Tris-HCl, pH 7.4 with 50 mM $MgCl_2$. A 50 µL reaction mixture, containing kinase buffer (50 mM Tris-HCl, pH 7.5, 10 mM $MgCl_2$, 1 mM EGTA, 0.01% Brij-35, 2 mM DTT, and 1× Complete protease inhibitor), 10 µM ATP (unless otherwise specified), and variable concentrations of purified kinase or cell lysates, was incubated with beads for up to 60 m.

Lysates prepared from cells distributed in sterile 96-well filter plates were diluted approximately five-fold for activity assays, while lysates prepared in conical tubes were diluted ten- to fifty-fold. Kinase reactions were terminated by the addition of 250 mM EDTA, pH 8.0. Three 5 m washes with 2% SDS and 5 successive washes with water were used to remove non-specific adsorption and detergent. 1 h incubation with 1% BSA in Tris-buffered saline with Tween-20 (TBST; 20 mM Tris base, 137 mM NaCl, 0.1% Tween-20, pH 7.6) was used to block non-specific binding of labeling antibodies.

Phosphorylated substrate was labeled sequentially with a 1:1000 dilution of biotinylated 4G10 and a 1:1000 dilution of phycoerythrin-coupled streptavidin in TBST. Beads were given a final wash with TBST and re-suspended in the Luminex system running buffer prior to analysis. All steps, including bead handling and labeling, were performed in reduced lighting.

Statistical Analysis

Several parameters were recorded for each bead region analyzed: the number of beads per region in the queried sample, the median, the mean, and the standard deviation of bound phycoerythrin per bead region. Data were reviewed using widely accepted methods of statistical inference (Snedecor and Cochran 1989). The following is the standard calculation procedure for the confidence interval and the standard error (Huntsberger and Billingsley 1987). Tables of t-values used in the calculation of the confidence interval were verified against published data from standard sources (Owen 1965; Snedecor and Cochran 1989).

$$\text{Confidence interval} = \frac{(X - t_{\frac{\alpha}{2}}, n-1) \times \sigma}{\sqrt{n}}$$

$$\text{Standard error} = \frac{\sigma}{\sqrt{n}}$$

where:

X=the mean fluorescence intensity per bead region per well $t_{\alpha/2}$=2-tailed t distribution, for a specified level of confidence ($\alpha$)

$_{n-1}$=degrees of freedom (df), sampled bead count per region per well minus one $\sigma$=standard deviation of the fluorescence intensity per bead region per well n=sample size, the number of beads sampled per bead region per well Because of variations in sample sizes, it was necessary to calculate confidence intervals based on specific t-values for each bead region in each well of a 96-well plate. The sampled number of beads per region per well was often less than 200, resulting in t-values that were substantially different from the normal distribution. Therefore, separate t-values were derived based on the sample size (n) for each bead region in each well, using published extended values for the t-distribution with six significant digits for df from 40 to 200 within one well (Owen 1965) and 4 significant digits for df from 500 to 10,000 over an entire plate (Federighi 1959).

Non-Linear Regression

Well-specific standard curves were constructed from the observed mean fluorescence intensity of known ratios of synthetically phosphorylated Abltide. Prism v4.0a (Graph-Pad Software, Inc., La Jolla, Calif., USA) was used to calculate the goodness of fit to non-linear models, where the criterion for selection was the minimum absolute sum of squares. For comparison, the correlation coefficient, $R^2$, was also noted. The Boltzmann-sigmoidal model best fit all of the data from acquired standard curves, with a calculated least squares of zero and an $R^2$ no less than 0.95. To calculate the effect of inhibitors on the observed fluorescence intensity and the calculated percentages of phosphorylation, sigmoidal curves (variable slope) provided an excellent fit after log-transformation of x-axis values, with an $R^2$ of 0.89-0.99. For kinetic rate relationships, such as the amount of enzyme units versus percent phosphorylation, or the lapse of reaction time versus phosphorylation, the best fit was either linear for short time scales or hyperbolic for extended concentrations or durations.

Spreadsheet

The instant application contains a copy of a spreadsheet herein referred to as "spreadsheet" which has been submitted in ASCII file format via EFS-Web and is hereby incorporated by reference in its entirety. Said ASCII file, created on Sep. 8, 2017, is named SPREADSHEETTXT and is 29 kilobytes in size. The spreadsheet contains a format and sequence of computer instructions useful for processing of equipment data output into statistically significant data for functional curves. The data in the spreadsheet is an exhibition of results from flow cytometry measurements using internal controls, with detailed calculations of the confidence level for each measurement based on statistical inference.

LENGTHY TABLES

The patent contains a lengthy table section. A copy of the table is available in electronic form from the USPTO web site (http://seqdata.uspto.gov/?pageRequest=docDetail&DocID=US10192030B2). An electronic copy of the table will also be available from the USPTO upon request and payment of the fee set forth in 37 CFR 1.19(b)(3).

CONCLUSIONS

The test protocol described herein results in a carefully calibrated internal standard for each well in the array. Significantly, this protocol allows substantially improved accuracy for use of microsphere arrays, so that standard statistical methods can be used to establish the level of confidence in the test results. The usefulness of this invention is established by providing a method that could impact human health by integrating basic biology with clinical science. The subject novel method can allow expansion of simultaneous high-accuracy quantitative analysis to one hundred or more kinase activities in a single experiment. The limitations as to number of kinase activities tested in a single experiment depend on the number of wells in the array, the number of available substrates, and the capacity of the equipment, but not on the subject method.

Those skilled in the art will recognize, or be able to ascertain using no more than routine experimentation, many equivalents to the specific embodiments of the invention described herein. Such equivalents are intended to be encompassed by the following claims. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

What is claimed is:

1. A method for quantifying enzyme activity, comprising:
   (a) contacting samples, wherein each of the samples may contain an enzyme, with a substrate under conditions in which the enzyme, when present in each sample, converts the substrate into a product, thereby generating reactions;
   (b) contacting each of the reactions with a set of internal standards, wherein each of the internal standards includes a different amount of product;
   (c) simultaneously quantifying under identical conditions, after (b), the amount of product converted from the substrate and the amount of each of the internal standards in each of the reactions;

(d) generating a standard curve for each of the reactions from the internal standards in each of the reactions; and (e) quantifying enzyme activity for each of the reactions according to each of the standard curves for each of the reactions.

2. The method of claim 1, wherein generating the standard curve in (d) comprises fitting a mathematical function to the amounts of the internal standards for each of the reactions.

3. The method of claim 1, wherein the standard curve is generated in (d) from more than one internal standard in each of the reactions.

4. The method of claim 3, wherein the standard curve is generated in (d) from four or more internal standards in each of the reactions.

5. The method of claim 1, wherein quantifying the enzyme activity in (e) comprises determining a mean and a confidence interval for the mean.

6. The method of claim 5, wherein the enzyme activity is quantified in (e) with a confidence interval at a 0.01 level of significance.

7. The method of claim 5, wherein quantifying the enzyme activity in (e) comprises analyzing three nominally identical reactions.

8. The method of claim 1, wherein the enzyme activity is quantified without replicates for each sample.

9. The method of claim 1, wherein each of the reactions is in a bead array or a chip array.

10. The method of claim 1, wherein each of the reactions is in a reaction vessel.

11. The method of claim 10, wherein the reaction vessel is a well in an array of wells.

12. The method of claim 1, wherein the substrate is bound to a bead and each of the internal standards is bound to a bead.

13. The method of claim 12, wherein the substrate and each of the internal standards each are bound to a different bead region.

14. The method of claim 13, wherein beads bound to the substrate and beads bound to each of the internal standards are quantified separately.

15. The method of claim 12, wherein each of the beads displays an internal fluorescence.

16. The method of claim 12, wherein the substrate comprises a synthetic peptide, the product comprises modified synthetic peptide and each of the internal standards comprise the modified synthetic peptide, wherein the enzyme modifies the synthetic peptide to generate the modified synthetic peptide.

17. The method of claim 16, wherein the synthetic peptide and the modified synthetic peptide are covalently bound to the beads.

18. The method of claim 17, wherein the synthetic peptide for the product and the synthetic peptide for the substrate are mixed in known molar ratios for the internal standards.

19. The method of claim 17, wherein the enzyme is a protein kinase, the product comprises phosphorylated peptide, and the internal standards each comprise different amounts of the phosphorylated peptide.

20. The method of claim 19, wherein activity of the enzyme is terminated after (a) and prior to (b).

21. The method of claim 20, wherein the quantifying in (c) comprises contacting the beads with an antibody that specifically binds to the phosphorylated peptide and comprises a fluorophore.

22. The method of claim 21, wherein the antibody specifically binds to phospho-tyrosine.

23. The method of claim 21, wherein the quantifying in (c) comprises separating the beads by flow cytometry and quantifying fluorescence emitted by the fluorophore of the antibody bound to the beads.

24. The method of claim 1, wherein the reactions comprise an inhibitor of the enzyme activity.

25. The method of claim 1, wherein quantifying the enzyme activity in (e) comprises quantification by mass spectrometry or liquid chromatography.

26. The method of claim 1, comprising determining a count of the number of components of a reaction, attaining a score for each of the components, and determining a confidence interval for each reaction.

27. The method of claim 26, comprising grouping identical reactions into a strata and determining statistics for each strata.

28. The method of claim 26, wherein:
each of the reactions is a well in an array of wells;
the substrate is bound to a bead;
each of the internal standards is bound to a bead;
each bead displays an internal fluorescence; and
each score is the measured fluorescence at the surface of each bead.

* * * * *